United States Patent [19]

Kristianson et al.

[11] Patent Number: 5,686,451
[45] Date of Patent: Nov. 11, 1997

[54] COMBINATION OF AN ACE INHIBITOR AND A DIURETIC

[76] Inventors: J. Krister Kristianson, Olofsgatan 13, S-193 00, Sigtuna, Sweden; Per Wold-Olsen, 5 Round Top Rd. P.O. Box 61, Oldwick, N.J. 08858-0061

[21] Appl. No.: 526,142

[22] Filed: Sep. 5, 1995

Related U.S. Application Data

[63] Continuation of Ser. No. 312,163, Sep. 26, 1994, abandoned, which is a continuation of Ser. No. 129,557, Sep. 28, 1993, abandoned, which is a continuation of Ser. No. 849,554, Mar. 11, 1992, abandoned.

[51] Int. Cl.⁶ .............................. A61K 31/54; A61K 31/40
[52] U.S. Cl. ................................ 514/223.5; 514/423
[58] Field of Search .................... 514/223.5, 423

[56] References Cited

U.S. PATENT DOCUMENTS 5,256,687  10/1993  Becker et al. ............. 514/419

FOREIGN PATENT DOCUMENTS

| | | |
|---|---|---|
| B-62431/86 | 9/1986 | Australia . |
| B-48703/90 | 1/1990 | Australia . |
| 0 521 388 A1 | 7/1991 | European Pat. Off. . |
| 129251 | 4/1965 | New Zealand . |
| 217489 | 7/1990 | New Zealand . |
| 2 010 675 B | 12/1978 | United Kingdom . |

OTHER PUBLICATIONS

Andren, L., et al., "Enalapril with Either a Very Low or Low Dose of Hydrochlorothiazide is Equally Effective in Essential Hypertension", Journal of Hypertension, vol. 1(Suppl. 2), pp. 384–386 (1983).

Becker, R.H.A., et al., "Loop Diuretics Combined with ACE Inhibitor for Treatment of Hypertension: A Study with Furosemide, Piretanide, and Ramipril in Spontaneously Hypertensive Rats", Chemical Abstract, vol. 111(9), 70668H (1989).

MacGregor, G.A., et al., "Captopril in Essential Hypertension; Contrasting Effects of Adding Hydrochlorothiazide or Propranol", British Medical Journal, vol. 284, pp. 693–696 (1982).

Brunner, H.R. et al., "Enhancement By Diuretics of the Antihypertensive Action of Long-Term Angiotensin Converting Enzyme Blockadet", Clinical and Experimental Hypertension, vol. 2(3 & 4), pp. 639–657 (1980).

Pollare, et al., "A Comparison of the Effects of Hydrochlorothiazide and Captopril on Gluccose and Lipid Metabolism in Patients with Hypertension", The New England J. of Med., vol. 321 (13), pp. 868–873, 1989.

Pool, et al., "Controlled Multicenter Study of the Antihypertensive Effects of Lisinopril, Plus Hydrochlorothiazide in the Treatment of 394 Patients with Mild to Moderate Essential Hypertension", J. of Cardio, Phamacol., vol. 9 (Suppl. 3), pp. S36–S42, 1987.

Jounela, et al., "Relation Between Low Dose of Hydrochlorothiazide, Antihypertensive Effect and Adverse Effects", Blood Pressure, vol. 3, pp. 231–235, 1994.

Guul, S.J., et al., "The Efficacy and Tolerability of Enalapril in a Formulation With a Very Low Dose of Hydrochlorothiazide in Hypertensive Patients Resistent to Enalapril Monotherapy", American Journal of Hypertension, Ltd., vol. 8, pp. 727–731 (1995).

New From MSD Research: "A novel therapeutic approach for the treatment of hypertension", Promotional material for Zynetec (1996).

Physicians' Desk Reference, 50th Edition, pp. 742–745, 837–840, 1737–1741, 1765–1768, 2851–2855, (1996).

*Primary Examiner*—Kimberly Jordan
*Attorney, Agent, or Firm*—Valerie J. Camara; Mark R. Daniel

[57] ABSTRACT

Pharmaceutical formulations comprising as active ingredients an angiotensin converting enzyme (ACE) inhibitor at a dose level normally found effective as an antihypertensive and a diuretic at a dose level below its minimum effective dose, demonstrate greater efficacy than would be expected in returning the blood pressure of hypertensive patients to normotensive values.

2 Claims, No Drawings

COMBINATION OF AN ACE INHIBITOR AND A DIURETIC

This is a continuation of application Ser. No. 08/312,163 filed on Sep. 26, 1994, now abandoned which, is a continuation of application Ser. No. 08/129,557, filed Sep. 28, 1993, now abandoned, which is a continuation of application Ser. No. 07/849,554 filed on Mar. 11, 1992, now abandoned.

BACKGROUND OF THE INVENTION

Both diuretics and ACE-inhibitors have an effect on the renin-angiotensin-aldosterone system. ACE-inhibitors act by inhibiting the conversion of angiotensin I to angiotensin II. Diuretics regulate the sodium-balance, and thereby also fluid volume. The decrease, both in sodium as well as volume, following therapy with diuretics increases plasma renin activity and thereby activates the renin-angiotensin-aldosterone system. This effect will to some degree counteract the blood-pressure lowering effect of the diuretic. When a diuretic and an ACE-inhibitor are combined the different pharmacological actions of these two drugs will, influence the effect of the other. There is accordingly a logical rationale for combining these two pharmacological principles.

It is possible to establish the highest non-pharmacological active dose of diuretic, i.e. a dose that is so low that it has no effect on blood pressure, and no apparent adverse effects. The highest non-effective dose of diuretic will still trigger the renin-angiotensin-aldosterone system and although it has no physiological effect of it's own, it will nonetheless have a potentiating effect on an ACE-inhibitor.

In a recently completed study by us of the effects of different doses of HCTZ on blood pressure and various metabolic parameters, doses ranging from 3 mg to 25 mg were investigated. 25 mg HCTZ produced significant effects on blood pressure and the metabolic parameters. 12.5 mg of HCTZ was found to be at the threshold of an effective antihypertensive response, and changes were seen in the metabolic parameters. Contrary to this, the doses of 3 and 6 mg were demonstrated not to be different from placebo in effects on blood pressure and various metabolic parameters.

Based on this study it can be concluded that 6 mg has been established as the highest non-pharmacological dose of HCTZ.

In a study by Andren et al., J. Hypertension 1 (suppl. 2) 384–386 (1983) doses of 6.25, 12.5 and 25 mg of hydrochlorothiazide (HCTZ) were combined with 10 and 40 mg of enalapril respectively. The authors concluded that: "the five combinations were equally effective in reducing blood pressure, and when given with enalapril the dose of HCTZ can be very low". When the Andren study was performed, it was not known by him that 6.25 mg is or is close to the non-pharmacological dose.

SUMMARY OF THE INVENTION

This invention is concerned with pharmaceutical formulations for the treatment of essential hypertension and disorders associated therewith such as congestive heart failure which have as active ingredients an angiotensin converting enzyme (ACE) inhibitor and a diuretic wherein the diuretic is at a dose level below the recognized pharmacological dose.

With these formulations the ACE inhibitor is found to have greater efficacy in reducing elevated blood pressure to normal levels than it would have if used at the same dose in monotherapy. At the same time the diuretic is being administered at dose levels that would be ineffective as an antihypertensive if used alone and similarly ineffective in causing adverse reactions.

DETAILED DESCRIPTION OF THE INVENTION

The novel pharmaceutical formulations of this invention comprise: a pharmaceutical carrier; an ACE inhibitor at the dose level normally employed in monotherapy, which is usually about 5–50 mg, depending on the ACE inhibitor; and a diuretic at a dose level which is the highest non-pharmacological dose.

The formulation is designed for oral administration and is presented as tablets, capsules, gel caps, caplets or as a sustained release formulation. It may also be designed as an elixir for oral administration, or a suppository for rectal administration.

Illustrative of the excipients which can be incorporated in tablets, capsules and the like are: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

The novel formulations of this invention are useful in the treatment of essential hypertension, and congestive heart failure.

The ACE inhibitors useful in the novel formulation and method of treatment of this invention are enalapril, lisinopril, captopril alacipril, benazapril, cilazapril, delapril, fosinopril, perindopril, quinapril, ramipril, moveltipril, spirapril, ceronapril, imidapril, temocapril, trandolopril, utilbapril, zofenopril, (R)-3-[(S)-1-carboxy-5-(4-piperidyl) pentyl]amino-4-oxo-2,3,4,5-tetrahydro-1,5-benzothiazepine-5-acetic acid, libensapril, zalicipril, n-octyl 2-[N-[(S)-1-ethoxycarbonyl-3-phenylpropyl]-L-alanyl]-(1S,3S,5S)-2-azabicyclo[3,3,0]octane -3-carboxylate maleate salt, 7-[(S)-1-carboxy-3-phenylpropyl)amino][4S-[4α,7α (R),12bβ]]-1,2,3,4,5,6,7,8,12b-octahydro-6-oxopyrido[2,1-a][2]benzazepine-4-carboxylic acid, N-[8-amino-1(S)-carboxyoctyl]-L-alanyl-L-proline, 3-pyridylcarbonyl-Lys-α-D-Glu-perhydroindole-2-carboxylic acid, benzhydryl[4α, 7α(R),12bβ]-7-[[1-(ethoxycarbonyl)phenylpropyl]amino]-1,2,3,4,6,7,12a,12b-octahydro-6-oxopyrido[2,1-a][2] benzazepine-4-carboxylate, 1-(N-((1S)-1-carboxy-3-phenylpropyl)-(S)-alanyl-4-(N-methyl-N-(6-chloro-7-sulfamoyl)-3,4-dihydro-1,2,4-benzothiadiazine-1,1-dioxide-3-yl)methyl)aminoproline.

Preferred ACE inhibitors are enalapril, lisinopril, captopril, perindopril, benzapril, quinapril, and cilazapril, especially enalapril.

The diuretics useful in the novel formulation and method of treatment of this invention are: hydrochlorothiazide (HCTZ), furosemide, altizide, trichlormethazide, triflumethazide, bemetizide, cyclothiazide, methylchlothiazide, azosemide, chlorothiazide, butizide, bendroflumethazide, cyclopenthiazide, benzclortriazide, polythiazide, hydroflumethazide, benzthiazide, ethiazide, penflutazide.

Preferred diuretics for incorporation in the novel formulation of this invention are hydrochlorothiazide, trichlormethazide, furosemide and altizide, especially hydrochlorothiazide.

In the specification and claims hereof, the naming of an ACE inhibitor or diuretic such as enalapril or hydrochlorothiazide respectfully is meant to include salts thereof such as enalapril maleate.

The novel method of treatment of this invention comprises the administration of a unit dose of the novel pharmaceutical formulation, one to three times a day depending on the patient and the severity of the indication being treated. Usually once or twice a day is adequate.

EXAMPLE 1

| Component | Amount (mg) | | |
|---|---|---|---|
| | A | B | C |
| enalapril maleate | 20 | 10 | 5 |
| hydrochlorothiazide | 6 | 6 | 6 |
| sodium bicarbonate | 10 | 5 | 2.5 |
| lactose | 154 | 164.1 | 198.1 |
| starch NF | 22 | 22 | 22.77 |
| pregelatinized starch NF | 2.2 | 2.2 | 5.06 |
| magnesium stearate | 1.1 | 1.0 | 0.90 |

The excipients shown in Example 1 are exemplary of the substituents used in each of the other examples that follow.

EXAMPLE 2

| Component | Amount (mg) | | |
|---|---|---|---|
| | 1 | 2 | 3 |
| lisinopril | 20 | 10 | 5 |
| hydrochlorothiazide | 6 | 6 | 6 |

EXAMPLE 3

| Component | Amount (mg) | | |
|---|---|---|---|
| | 1 | 2 | 3 |
| Captopril | 50 | 25 | 12.5 |
| hydrochlorothiazide | 6 | 6 | 6 |

EXAMPLE 4

| Component | Amount (mg) | | |
|---|---|---|---|
| | 1 | 2 | 3 |
| Benazapril | 40 | 20 | 10 |
| hydrochlorothiazide | 6 | 6 | 6 |

EXAMPLE 5

| Component | Amount (mg) | | |
|---|---|---|---|
| | 1 | 2 | 3 |
| Quinapril | 20 | 10 | 5 |
| hydrochlorothiazide | 6 | 6 | 6 |

EXAMPLE 6

| Component | Amount (mg) | | |
|---|---|---|---|
| | 1 | 2 | 3 |
| Cilazapril | 50 | 25 | 12.5 |
| hydrochlorothiazide | 6 | 6 | 6 |

What is claimed is:

1. A pharmaceutical formulation comprising a pharmaceutical carrier and dispersed therein 20 mg of enalapril maleate and 6 mg of hydrochlorothiazide.

2. A method of treating hypertension, which comprises the administration to a patient in need of such treatment a pharmaceutical formulation comprising 20 mg of enalapril maleate and 6 mg of hydrochlorothiazide.

* * * * *

UNITED STATES PATENT AND TRADEMARK OFFICE
CERTIFICATE OF CORRECTION

PATENT NO. : 5,686,451

DATED : Nov. 11, 1997

INVENTOR(S) : J. Krister Kristianson and Per Wold-Olsen

It is certified that error appears in the above-identified patent and that said Letters Patent is hereby corrected as shown below:

On cover page, insert item [73], to read --Merck & Co., Inc., Rahway, New Jersey--

Signed and Sealed this

Third Day of November, 1998

Attest:

BRUCE LEHMAN

Attesting Officer

Commissioner of Patents and Trademarks